United States Patent
Flohr et al.

(10) Patent No.: US 9,132,284 B2
(45) Date of Patent: Sep. 15, 2015

(54) CONTRAST AGENT-ENHANCED IMAGING DURING RADIATION THERAPY

(75) Inventors: Thomas Flohr, Uehlfeld (DE); Stefan Gleissmann, Erlangen (DE); Michael Grasruck, Nürnberg (DE); Raimund Martin, Eggolsheim/Bammersdorf (DE); Marcus Wagner, Obermichelbach (DE); Georg Wittmann, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 404 days.

(21) Appl. No.: 13/561,380

(22) Filed: Jul. 30, 2012

(65) Prior Publication Data

US 2013/0034212 A1 Feb. 7, 2013

(30) Foreign Application Priority Data

Aug. 3, 2011 (DE) .................. 10 2011 080 364

(51) Int. Cl.
*H05G 1/64* (2006.01)
*A61N 5/10* (2006.01)
*A61B 6/03* (2006.01)
*A61B 6/00* (2006.01)

(52) U.S. Cl.
CPC .............. *A61N 5/1049* (2013.01); *A61B 6/032* (2013.01); *A61B 6/481* (2013.01); *A61B 6/482* (2013.01); *A61B 6/4014* (2013.01); *A61B 6/4085* (2013.01); *A61B 6/487* (2013.01); *A61B 6/5217* (2013.01); *A61B 6/5235* (2013.01); *A61N 2005/1061* (2013.01)

(58) Field of Classification Search
CPC ...... A61B 6/4014; A61B 6/482; A61B 6/481; A61B 6/4007; A61B 6/466; A61B 19/50; A61B 2019/507; A61B 6/032; A61N 2005/1061; A61N 5/1049; A61N 5/103; A61N 5/1067; G01N 23/046; G01N 2223/419; G01N 2223/612; Y10S 378/901; G01T 1/2985; G06T 2207/10072; G06T 2207/30004; G06T 2211/408
USPC ............... 378/4, 5, 62, 65, 98, 128, 131, 132, 378/154; 600/4, 25, 427, 458
See application file for complete search history.

(56) References Cited

U.S. PATENT DOCUMENTS

| | | | |
|---|---|---|---|
| 5,207,223 A | 5/1993 | Adler | |
| 5,651,043 A * | 7/1997 | Tsuyuki et al. | 378/65 |
| 5,734,692 A | 3/1998 | Seki | |

(Continued)

FOREIGN PATENT DOCUMENTS

| | | |
|---|---|---|
| CN | 1768707 A | 5/2006 |
| CN | 1814323 A | 8/2006 |

(Continued)

OTHER PUBLICATIONS

Riedel, "an introduction to dual energy computed tomography" university of texas health Science center at san Antonio.*

*Primary Examiner* — Michael Logie
(74) *Attorney, Agent, or Firm* — Harness, Dickey & Pierce

(57) ABSTRACT

A method is disclosed for imaging within the scope of a radiation therapy. In at least one embodiment, the method includes preparing one or more contrast agent-enhanced x-ray image data records; and using the contrast agent-enhanced x-ray image data record during an irradiation planning and/or during an irradiation session.

12 Claims, 2 Drawing Sheets

(56) References Cited

U.S. PATENT DOCUMENTS

| | | | |
|---|---|---|---|
| 5,896,439 A * | 4/1999 | Krause et al. | 378/95 |
| 8,068,578 B2 | 11/2011 | Krauss | |
| 8,738,115 B2 * | 5/2014 | Amberg et al. | 600/427 |
| 2006/0067473 A1 | 3/2006 | Eberhard et al. | |
| 2006/0182326 A1 | 8/2006 | Schildkraut et al. | |
| 2006/0245537 A1 | 11/2006 | Bakai et al. | |
| 2007/0205367 A1 * | 9/2007 | Deman et al. | 250/363.02 |
| 2007/0217570 A1 * | 9/2007 | Grasruck et al. | 378/53 |
| 2008/0013674 A1 * | 1/2008 | Zhang et al. | 378/9 |
| 2009/0022263 A1 * | 1/2009 | Imai | 378/5 |
| 2009/0054772 A1 | 2/2009 | Lin et al. | |
| 2009/0086884 A1 * | 4/2009 | Krauss | 378/5 |
| 2010/0135557 A1 * | 6/2010 | Krauss et al. | 382/131 |
| 2010/0135565 A1 * | 6/2010 | Thomsen et al. | 382/132 |
| 2011/0064292 A1 * | 3/2011 | Chen et al. | 382/131 |
| 2011/0085640 A1 | 4/2011 | Fadler | |
| 2011/0135051 A1 * | 6/2011 | Fadler et al. | 378/4 |
| 2011/0166408 A1 * | 7/2011 | Sumanaweera et al. | 600/1 |
| 2012/0027162 A1 * | 2/2012 | Garnica Garza | 378/4 |

FOREIGN PATENT DOCUMENTS

| | | | | |
|---|---|---|---|---|
| CN | 1853566 A | 11/2006 | | |
| CN | 101237907 A | 8/2008 | | |
| CN | 102096905 A | 6/2011 | | |
| DE | 69529857 T2 | 1/2004 | | |
| DE | 102007046514 A1 | 4/2009 | | |
| DE | 102008034020 A1 * | 1/2010 | | A61N 5/10 |
| DE | 102009057066 A1 | 6/2011 | | |
| DE | 102009049074 B4 | 9/2011 | | |

* cited by examiner

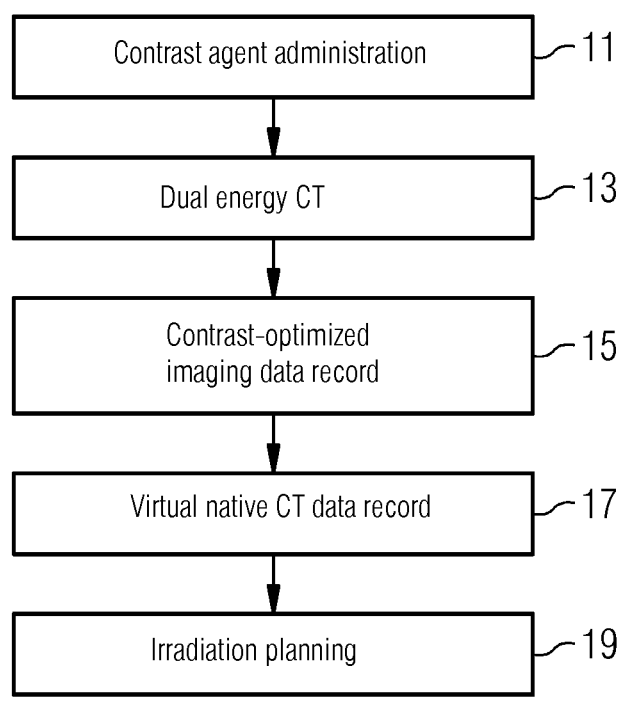

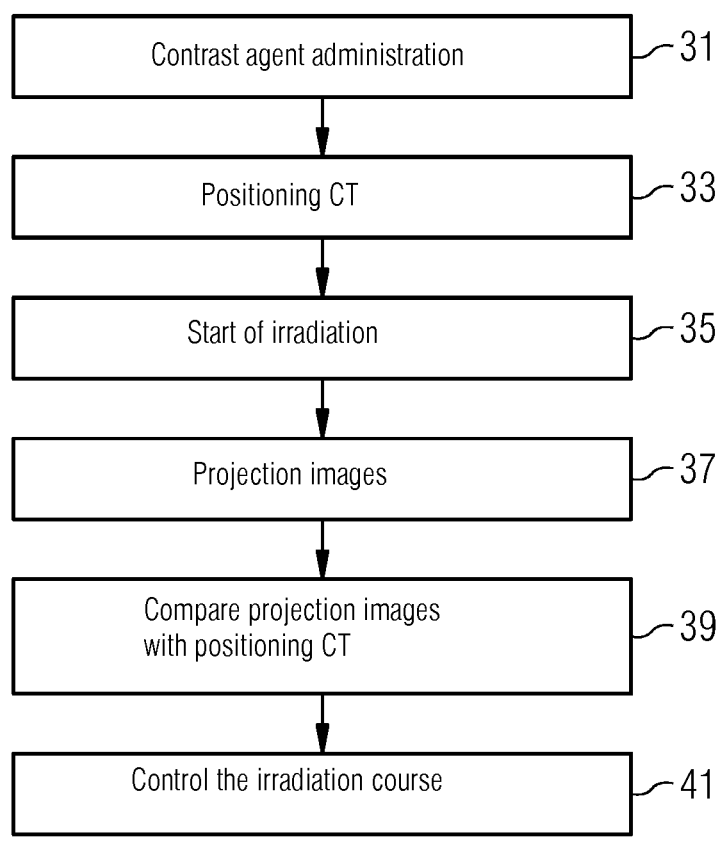

CONTRAST AGENT-ENHANCED IMAGING DURING RADIATION THERAPY

PRIORITY STATEMENT

The present application hereby claims priority under 35 U.S.C. §119 to German patent application number DE 10 2011 080 364.5 filed Aug. 3, 2011, the entire contents of which are hereby incorporated herein by reference.

FIELD

At least one embodiment of the invention generally relates to a method for imaging within the scope of a radiation therapy.

BACKGROUND

Radiation therapy is an established method in which ionizing radiation is used to treat pathological tissue, such as tumor issue for instance. The aim of radiation therapy is to irradiate the tissue to be treated with an adequate therapeutic dose and in the process simultaneously preserve healthy, surrounding tissue. The therapeutic effect is based inter alia on ionizing radiation acting differently on healthy tissue and on pathological tissue.

To ensure that uncertainties in the positioning of the tissue to be treated, which may occur between a planning phase and a treatment phase for different reasons, do not endanger the success of the treatment, safety margins are usually used in order to enlarge the target volume.

Image guided radiation therapy (IGRT) enables uncertainties in the irradiation of the target volume to be reduced. IGRT allows visualization of the target volume, organs at risk (OAR) and healthy, surrounding tissue prior to starting an irradiation so as in principle to enable the target volume to be irradiated more precisely and smaller safety margins to be used.

In order to be better able to determine patient changes between the fractions, a computed tomography recording (also CT for computed tomography) can be produced prior to each irradiation, ideally on the same couch. The position of the tumor can therefore be readjusted.

In order to observe the patient movement during the irradiation, the MV therapy beam can also be used for projection imaging, e.g. for so-called "portal imaging". Furthermore, systems also exist which in addition to the MV therapy beam, also have a further x-ray source and an additional x-ray-sensitive detector. Aside from projective monitoring of the patient movement, a CT imaging can therefore also be operated as a positioning control.

Sectional images are required in order to create irradiation plans for the radiation therapy, said sectional images representing the region to be irradiated in a three-dimensional fashion. To this end, CT images are predominantly used.

SUMMARY

At least one embodiment of the invention provides a method which ultimately results in an accurate and precise beam application.

Advantageous developments of the invention are found in the features of the dependent claims.

An embodiment of the inventive method for imaging within the scope of a radiation therapy includes,
    producing one (or more) contrast agent-enhanced x-ray image data records, and
    using the contrast agent-enhanced x-ray image data record during an irradiation planning and/or during an irradiation session.

BRIEF DESCRIPTION OF THE DRAWINGS

Embodiments of the invention having advantageous developments according to the features of the dependent claims are described in more detail with the aid of the following drawing, without being restricted thereto, in which:

FIG. 1 shows a flow chart of an irradiation planning method,

FIG. 2 shows a flow chart of a method which is used within the scope of an irradiation session.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An embodiment of the inventive method for imaging within the scope of a radiation therapy includes, producing one (or more) contrast agent-enhanced x-ray image data records, and using the contrast agent-enhanced x-ray image data record during an irradiation planning and/or during an irradiation session.

It was identified that the tissue to be irradiated and the surrounding area, if only shown natively, comprise a certain contrast, which is nevertheless lower since the contrast of a native image is naturally not especially high.

A good delimitation of diseased and healthy tissue is very advantageous for a reliable and in particular automated evaluation of the tissue to be irradiated e.g. for tumor identification.

In order to implement the x-ray imaging, a contrast agent is now provided for contrast-enhancement. A plurality of applications and work processes is conceivable. In the case of a liver, e.g. an image can be produced in the arterial phase, the venous phase or the subsequent venous phase. The general, improved delimitation of organs is nevertheless also maintained for a few minutes after administration of the contrast agent.

While native x-ray imaging, e.g. a native CT imaging, is not normally able to cancel a detailed soft tissue contrast, the combination with the contrast agent now also enables the tumor itself to be made visible in the therapy process. It is then possible to dispense with a connection via bones and correlated atlases, with which the tumor localization otherwise has to be implemented.

Embodiments of the invention are furthermore advantageous in that it is possible to dispense with so-called seeds or fiducials. Seeds/fiducials, in other words markers, are namely often used to better identify the tumor volume in the native image, and are therefore implanted for some space-occupying lesions. The seeds/fiducials are made of metallic connections and can therefore also be easily identified on a native image. The implantation of the seeds/fiducials is however an invasive intervention which involves all typical side effects (e.g. infections).

In one embodiment of the method, the contrast agent-enhanced x-ray image data record is a contrast agent-enhanced three-dimensional x-ray image data record, e.g. a computed tomography data record, which is recorded using a dual source computed tomograph. The irradiation planning is then implemented using this three-dimensional x-ray image data record.

It has been identified that sectional images are particularly advantageous for the creation of irradiation plans, on which the tissue to be irradiated and the healthy tissue to be treated with care can clearly be delimited from one another. Furthermore, the density of the tissue should only be precisely reproduced for precise dose planning.

The CT images usually used here, from which the density of the tissue can be inferred with the aid of so-called Hounsfield Units (HUs), are disadvantageous in terms of a low contrast. For organs which frequently differ only marginally from surrounding tissue in terms of their density, the contouring, i.e. the delimitation of the tumor area, is difficult and represents the largest uncertainty factor in therapy planning.

CT recordings which were created using contrast agent nevertheless offer an improved contrast, but no longer correctly represent the density of the tissue and are similarly less well-suited to dose planning. Incorrect density values (HUs) must then be replaced manually by means of tabular values for instance.

It is now possible to solve this problem by a single 3D x-ray recording being created with contrast agent, namely using a dual source computed tomograph (also known as dual source CT or dual energy CT).

Two different, further imaging data records can then be calculated from the dual energy computed tomography data record. These two imaging data records can then visualize different specific object properties respectively. The first imaging data record may therefore have a higher contrast than the second imaging data record. The second imaging data record may be a virtual native computed tomography data record (so-called "virtual native image").

The virtual native computed tomography data record can then be used to determine attenuation values for therapeutic radiation during the irradiation planning.

Two (or even more) different imaging data records can subsequently be calculated from this one dual energy CT recording or dual source CT recording on account of the different attenuation course of the two energy parts of the dual energy x-ray radiation. An imaging data record represents the optimal contrast with respect to tissue differentiation and a second imaging data record contains the correct density values. The HUs are so-to-speak therefore shown in a linear fashion. These different representations are based on the same recording and are therefore perfectly congruent and produced with minimal effort.

Instead of a dual source CT, a hybrid imaging system, including a single source computed tomograph and an imaging system with a separate x-ray radiation source and a separate 2-dimensional radiation detector, can also be used to record the three-dimensional contrast agent-enhanced x-ray image data record. The imaging system, e.g. a kV imaging system, can be embodied for instance to produce radiographic fluoroscopy recordings, of fluoroscopes and/or of cone beam computed tomographs.

It is similarly conceivable to use a hybrid imaging system, including two such imaging systems each with its own x-ray radiation source and 2-dimensional radiation detector, in order to record the three-dimensional contrast agent-enhanced x-ray image data record.

Even with such systems, virtual native recordings can be calculated from the three-dimensional x-ray image data record.

Contrary to solutions which are based on the creation of two separate recordings (with and without contrast agent), the patient is now no longer exposed to an additional radiation dose. The risk of the two recordings not being able to fuse precisely, i.e. by moving between the two recording time instances, is reduced.

Contrary to solutions in which a CT recording with the recordings from other imaging methods (e.g. MRT, ultrasound, PET) are fused in order to achieve improved tumor localization, the precise tumor localization is now achieved with a single dual energy CT recording.

In an embodiment of the method, the contrast agent-enhanced x-ray image data record is registered during an irradiation session for localization of the target volume.

The idea is now to use the improved diagnostic information, which is possible by administering the contrast agent, in the time range in which the irradiation usually takes place (generally a few minutes), in order on the one hand to be better able to control the therapy beam and if necessary to be able to respond to deviations relating to the planning.

A computed tomography imaging is advantageous herefor, which is clearly quicker than the overall duration of radiotherapy. In each case, the optimized imaging can be used for quality control by way of the entire therapy session.

Even with radiation therapy systems in which the imaging is implemented using flat panel detectors, this results in a decisive advantage since flat panel detectors usually have a limited image quality.

The irradiation session may in particular be an irradiation session of a hyperfractionated irradiation or a single fraction irradiation.

A conventional fractionated radiation therapy is often applied to 25 to 30 fractions with one fraction per day. A therapeutic advantage should be weighed up here by the use of the contrast agent compared with the possible side effects of the contrast agent (e.g. renal failure).

It was however identified that this is therapeutically advantageous upon a change in the fractionation, e.g. upon a hypofractionation (up to 5 fractions with considerably higher individual doses) or with a so-called "single-fraction"-therapy. This embodiment of the method is therefore particularly advantageous here.

The administration of the contrast agent can be coordinated with the time instant of the irradiation session such that the contrast agent dispenses with its contrast-enhancing property for the duration of the irradiation session. This can occur by the contrast agent being administered immediately prior to the start of the irradiation session.

The contrast agent-enhanced image data record may be a computed tomography data record registered prior to the start of the irradiation session in order to position the patient, said data record being produced for instance to position the patient. In this case, a further contrast agent-enhanced x-ray image data record (e.g. a two-dimensional projection image) can be registered during the course of the irradiation, which is automatically compared with the computed tomography data record with the aid of a computing unit.

The recordings can be evaluated very quickly online during the irradiation. This can now take place fully automatically by means of a computing unit. The computing unit can detect and segment the tumor automatically and reliably in order to be able to derive a decision from the comparison which is then used in turn to control the irradiation. The contrast agent-enhanced imaging significantly facilitates methods of this type, since the localization of the tumor and the comparison of images can now essentially be implemented in a simpler and more precise fashion.

FIG. 1 shows a flow chart of an irradiation planning.

A contrast agent is initially administered to the patient (step 11).

A dual energy CT data record having a dual energy CT is then registered (step 13). Two further imaging data records are determined from this data record.

The first imaging data record (step 15) has an optimal contrast for tumor localization and to delimit organs at risk.

The second imaging data record (step 17) is a virtual native CT image data record. This means that the density values correspond to the density values of a native CT, although a contrast agent was administered to the patient upon registration of the raw image data.

The irradiation planning is then implemented with the aid of these two data records (step 19).

The first imaging data record is used to localize and segment the target organs and the structures to be treated gently. The second imaging data record is used to take into account and determine the correct attenuation of the therapeutic radiation during the irradiation planning. Implementation of the irradiation planning is then carried out using known methods. The finished irradiation plan is stored or transferred to a radiation therapy device.

FIG. 2 shows a flow chart of a method, which is used during an irradiation session.

Immediately prior to the start of an irradiation sessions, which may be an irradiation session of a hypofractionated irradiation or a single fraction irradiation, a contrast agent is administered to the patient (step 31).

A first computed tomography is implemented, which is then used to position the patient in respect of the radiation therapy device (step 33). The tumor is herewith positioned in the isocenter such that, as planned, it can be irradiated.

The irradiation is started (step 35).

During the course of the irradiation, further two-dimensional projection image data is produced (step 37), which is automatically compared with the positioning CT online, i.e. still during the irradiation, by way of a computing unit (step 39).

As a function of the comparison, the course of the irradiation is controlled (step 41). The irradiation can therefore be interrupted if an excessively large deviation is produced between the projection image data and the positioning CT. The irradiation can however also be modified in order to balance out any changes.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for imaging an organ of a patient using an imaging device, within a scope of a radiation therapy, comprising:
    obtaining, by a processor of the imaging device, a contrast agent-enhanced x-ray image data record; and
    determining a first image data record and a second image data record based on the contrast agent-enhanced x-ray image data record, the first image data record identifying the organ of the patient and the second image data record indicating a correct attenuation of therapeutic radiation;
    controlling, by the processor, an irradiation planning session and an irradiation session for the patient using the first image data record and the second image data record.

2. The method of claim 1, wherein the contrast agent-enhanced x-ray image data record is a three-dimensional contrast agent-enhanced x-ray image data record registered with a dual source computed tomography.

3. The method of claim 1, wherein the contrast agent-enhanced x-ray image data record is a three-dimensional contrast agent-enhanced x-ray image data record registered with a hybrid imaging system, including a single source computed tomography and an imaging system with a separate x-ray radiation source and a separate 2-dimensional radiation detector.

4. The method of claim 1, wherein
    the obtaining obtains the contrast agent-enhanced x-ray image data record, with a hybrid imaging system including two imaging systems, each imaging system including an x-ray radiation source and a 2-dimensional radiation detector, and
    the contrast agent-enhanced x-ray image data record is a registered three-dimensional contrast agent-enhanced x-ray image data record.

5. The method of claim 1, wherein
    the first image data record has a higher contrast than the second imaging data record, and
    the second imaging data record is a virtual native computed tomography data record.

6. The method of claim 5, wherein the virtual native computed tomography data record is used to determine attenuation values for the therapeutic radiation during the irradiation planning.

7. The method of claim 1, wherein the contrast agent-enhanced x-ray image data record is registered during an irradiation session for localization of the organ of the patient.

8. The method of claim 7, wherein the irradiation session is an irradiation session of a hypofractionated irradiation or a single fraction irradiation.

9. The method of claim 8, wherein an administration of the contrast agent is coordinated with a time instant of the irradiation session such that the contrast agent dispenses a contrast-enhancing property for a duration of the irradiation session.

10. The method of claim 7, wherein an administration of the contrast agent is coordinated with a time instant of the irradiation session such that the contrast agent dispenses a contrast-enhancing property for a duration of the irradiation session.

11. The method of claim 1, wherein
    the contrast agent-enhanced x-ray image data record is a computed tomography data record registered prior to a start of the irradiation session, for positioning the patient, and
    during the irradiation session, a further contrast agent-enhanced x-ray image data record is registered, which is automatically compared with the computed tomography data record via a computing unit.

12. A non-transitory computer readable medium including computer-readable program product, the computer-readable program product comprising instructions, which when executed on a computer device, causes the computer device to implement the method of claim 1.

* * * * *